US008852271B2

(12) United States Patent
Murray, III et al.

(10) Patent No.: US 8,852,271 B2
(45) Date of Patent: Oct. 7, 2014

(54) TRANSCATHETER PROSTHETIC HEART VALVE DELIVERY DEVICE WITH BIASED RELEASE FEATURES

(75) Inventors: Robert J. Murray, III, Santa Rosa, CA (US); Jason Kolden, Byron Center, MI (US); Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 396 days.

(21) Appl. No.: 13/095,117

(22) Filed: Apr. 27, 2011

(65) Prior Publication Data

US 2011/0264202 A1 Oct. 27, 2011

Related U.S. Application Data

(60) Provisional application No. 61/328,328, filed on Apr. 27, 2010.

(51) Int. Cl.
  *A61F 2/84* (2006.01)
  *A61F 2/966* (2013.01)
  *A61F 2/24* (2006.01)
  *A61F 2/95* (2013.01)

(52) U.S. Cl.
  CPC .............. *A61F 2/2418* (2013.01); *A61F 2/966* (2013.01); *A61F 2002/9505* (2013.01); *A61F 2/2436* (2013.01)
  USPC ........................................ 623/2.11; 623/1.11

(58) Field of Classification Search
  USPC ............... 623/1.11–1.12, 2.11; 606/191–195, 606/198, 200
  See application file for complete search history.

(56) References Cited

U.S. PATENT DOCUMENTS

| 5,415,664 | A | * | 5/1995 | Pinchuk ...................... 623/1.11 |
| 5,683,451 | A | | 11/1997 | Lenker et al. |
| 5,824,041 | A | | 10/1998 | Lenker et al. |
| 5,906,619 | A | | 5/1999 | Olson et al. |
| 5,957,949 | A | | 9/1999 | Leonhardt et al. |
| 8,062,349 | B2 | * | 11/2011 | Moore et al. ................. 623/1.34 |
| 8,246,678 | B2 | * | 8/2012 | Salahieh et al. ............. 623/2.11 |
| 8,398,694 | B2 | * | 3/2013 | Forde et al. ................. 623/1.11 |
| 8,414,640 | B2 | * | 4/2013 | Schmitt et al. ............... 623/1.23 |
| 8,414,645 | B2 | * | 4/2013 | Dwork et al. ................ 623/2.11 |
| 2003/0199963 | A1 | | 10/2003 | Tower et al. |

(Continued)

FOREIGN PATENT DOCUMENTS

GB 2433700 7/2007
WO WO2008/138584 11/2008

(Continued)

*Primary Examiner* — Mark Mashack

(57) ABSTRACT

A delivery system for percutaneously delivering and deploying a stented prosthetic heart valve. The delivery device includes a delivery sheath slidably disposed over an inner shaft, and a capture assembly. The capture assembly includes a spindle and a biasing member. The spindle is attached to the inner shaft and defines slot. The biasing member is disposed within the slot and self-transitions from a deflected condition to a normal condition. In a delivery state, the delivery sheath retains the prosthesis over the inner shaft and coupled to the spindle via the capture slot, including a portion of the prosthetic valve being engaged within the slot and the biasing member forced to the deflected condition. In a deployment state, the delivery sheath is proximally withdrawn and the biasing member self-transitions toward the normal condition to eject the prosthetic valve from the capture slot.

22 Claims, 15 Drawing Sheets

(56) References Cited

U.S. PATENT DOCUMENTS

| | | |
|---|---|---|
| 2004/0093063 A1* | 5/2004 | Wright et al. ............... 623/1.12 |
| 2005/0049667 A1* | 3/2005 | Arbefeuille et al. ......... 623/1.11 |
| 2005/0137688 A1 | 6/2005 | Salahieh et al. |
| 2006/0004439 A1 | 1/2006 | Spenser et al. |
| 2006/0052867 A1 | 3/2006 | Revuelta et al. |
| 2006/0253184 A1* | 11/2006 | Amplatz ...................... 623/1.11 |
| 2006/0259136 A1 | 11/2006 | Nguyen et al. |
| 2006/0265056 A1 | 11/2006 | Nguyen et al. |
| 2007/0005131 A1 | 1/2007 | Taylor |
| 2007/0043420 A1* | 2/2007 | Lostetter ...................... 623/1.11 |
| 2007/0088431 A1 | 4/2007 | Bourang et al. |
| 2007/0239266 A1 | 10/2007 | Birdsall |
| 2007/0239269 A1 | 10/2007 | Dolan et al. |
| 2008/0065011 A1 | 3/2008 | Marchand et al. |
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2008/0262590 A1* | 10/2008 | Murray ........................ 623/1.11 |
| 2009/0093876 A1 | 4/2009 | Nitzan et al. |
| 2009/0138079 A1 | 5/2009 | Tuval et al. |
| 2009/0171447 A1 | 7/2009 | Von Segesser et al. |
| 2009/0177275 A1 | 7/2009 | Case |
| 2009/0198318 A1* | 8/2009 | Berez et al. .................. 623/1.11 |
| 2009/0276027 A1* | 11/2009 | Glynn .......................... 623/1.11 |
| 2009/0281619 A1 | 11/2009 | Le et al. |
| 2009/0287290 A1* | 11/2009 | Macaulay et al. ........... 623/1.11 |
| 2010/0094411 A1 | 4/2010 | Tuval et al. |
| 2010/0121434 A1 | 5/2010 | Paul et al. |
| 2010/0191326 A1* | 7/2010 | Alkhatib ...................... 623/2.11 |
| 2010/0292782 A1* | 11/2010 | Giannetti et al. ............ 623/2.11 |
| 2011/0251682 A1* | 10/2011 | Murray et al. ............... 623/2.11 |
| 2013/0204356 A1* | 8/2013 | Dwork et al. ................ 623/2.11 |

FOREIGN PATENT DOCUMENTS

| | | |
|---|---|---|
| WO | WO2009/091509 | 7/2009 |
| WO | WO2009/124124 | 10/2009 |
| WO | WO2011/025945 | 3/2011 |

\* cited by examiner

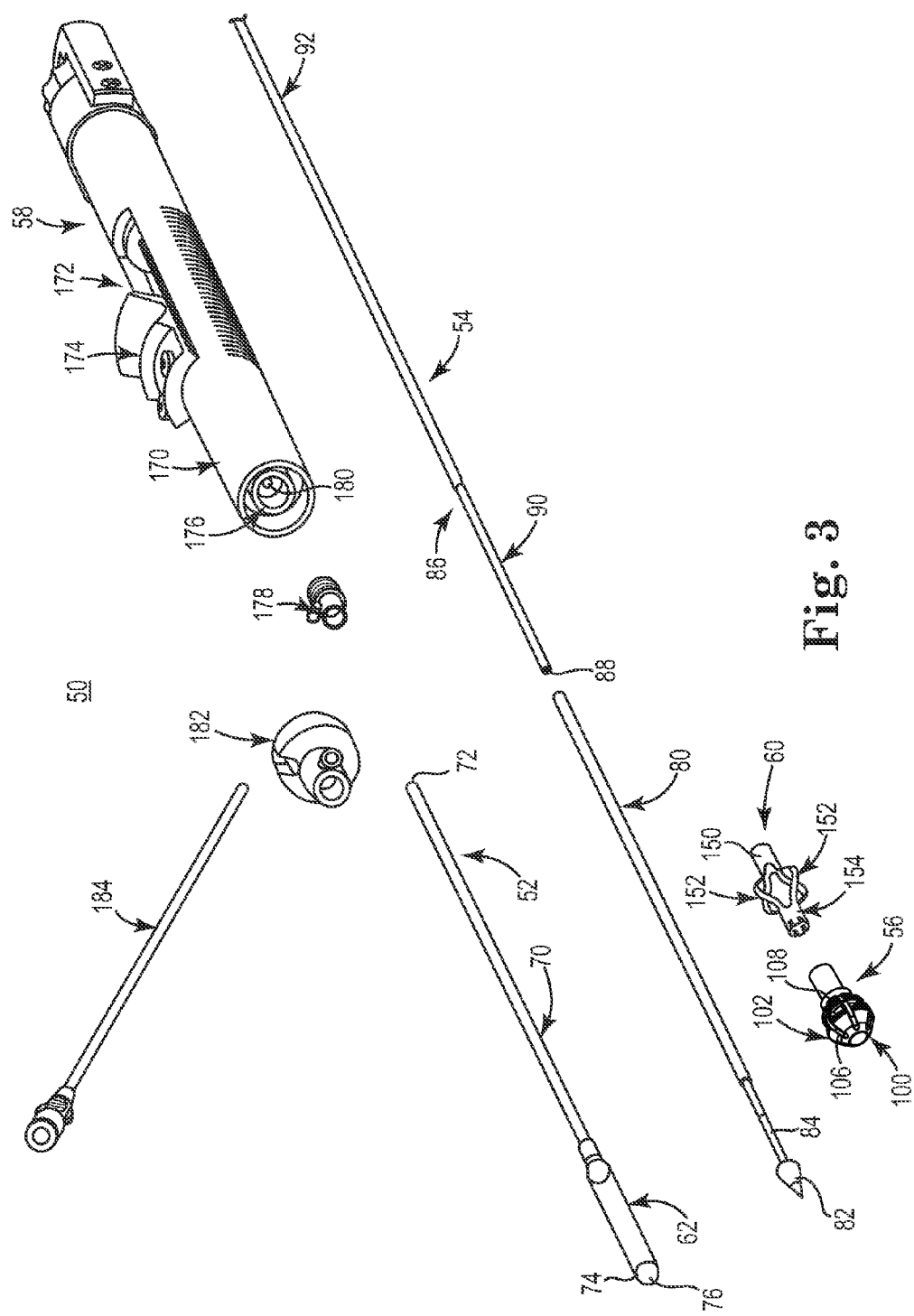

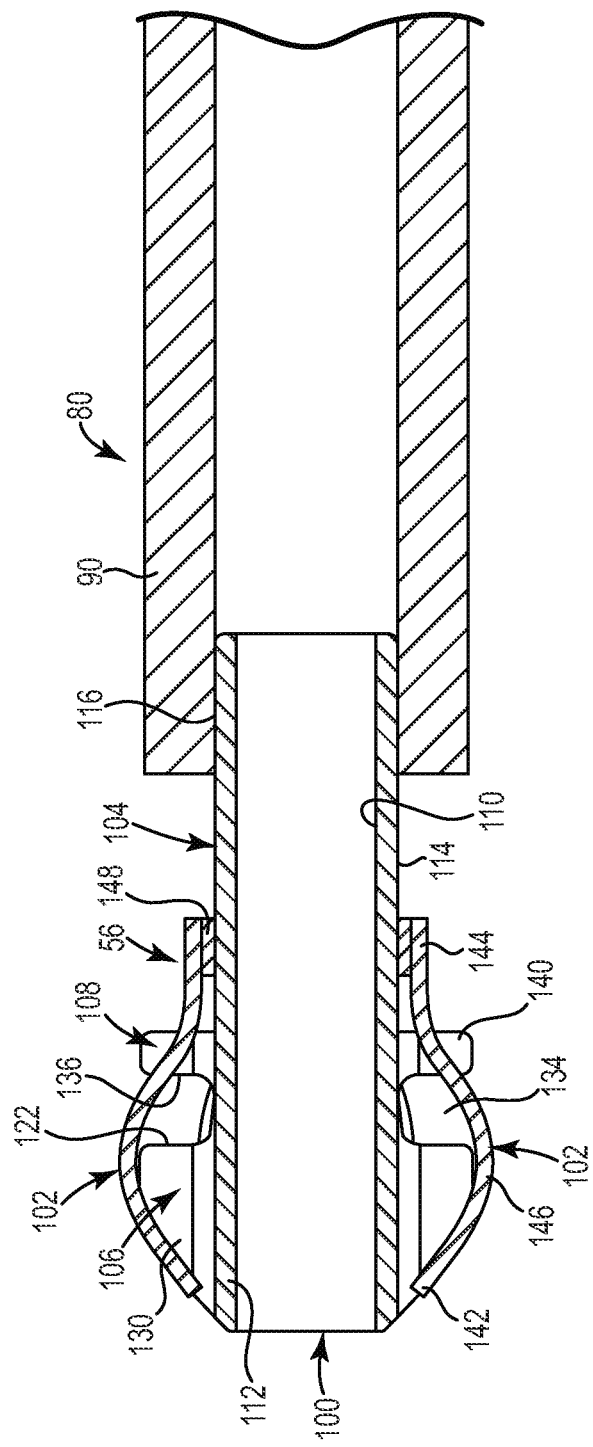

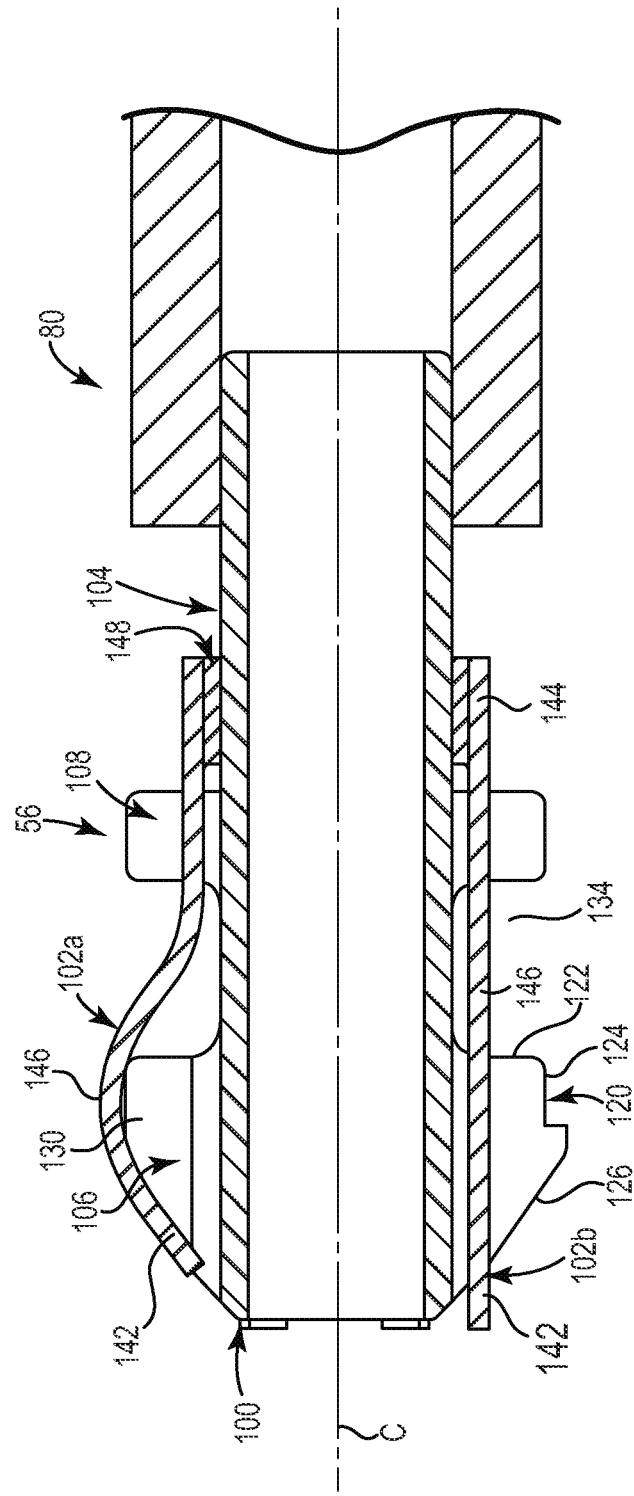

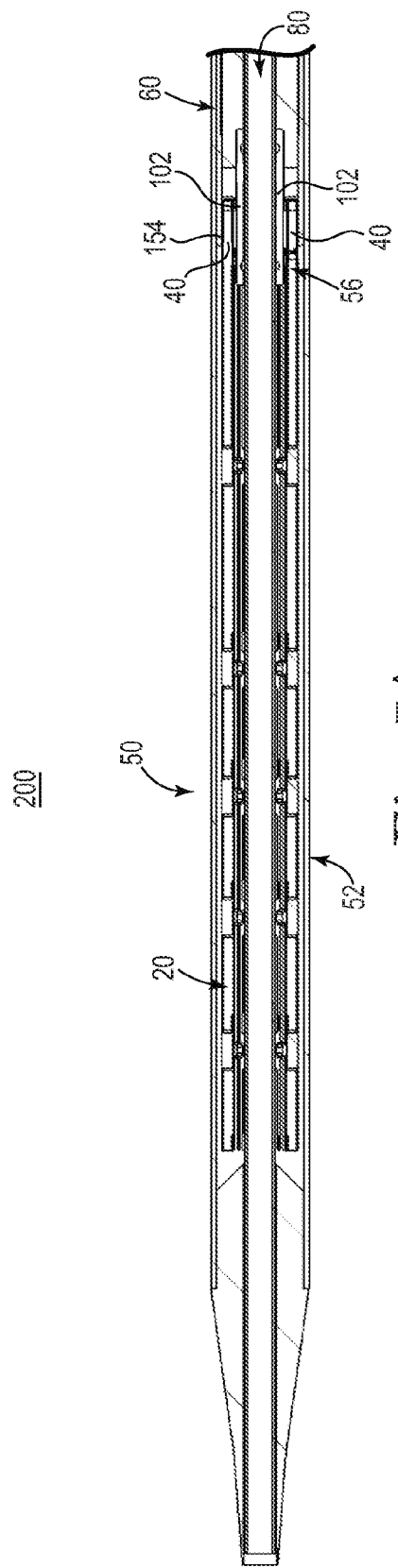

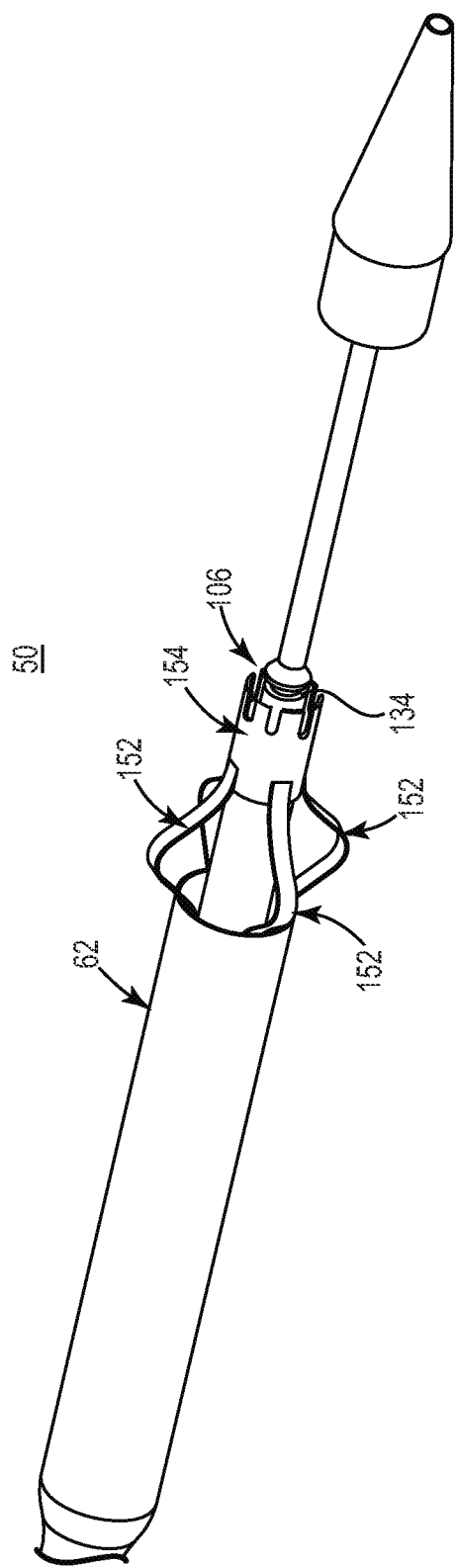

TRANSCATHETER PROSTHETIC HEART VALVE DELIVERY DEVICE WITH BIASED RELEASE FEATURES

CROSS-REFERENCE TO RELATED APPLICATIONS

This application claims priority under 35 U.S.C. §119(e)(1) to U.S. Provisional Patent Application Ser. No. 61/328,328, filed Apr. 27, 2010, entitled "Transcatheter Prosthetic Heart Valve Delivery Device with Biased Release Features", and bearing; the entire teachings of which are incorporated herein by reference.

BACKGROUND

The present disclosure relates to systems, devices, and methods for percutaneous implantation of a prosthetic heart valve. More particularly, it relates to delivery systems, devices, and methods for transcatheter implantation of a stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being replaced (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. The so-loaded balloon catheter is slidably disposed within an outer delivery sheath. Once delivered to the implantation site, the balloon is inflated to deploy the prosthesis. With either of these types of percutaneous stented prosthetic valve delivery devices, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

To carefully and safely deploy a transcatheter prosthetic heart valve, a clinician can employ imaging technology to evaluate the location of the prosthesis immediately prior to deployment. In particular, one desirable transcatheter prosthetic heart valve implantation technique entails partially deploying a distal region of the prosthesis from the delivery device and then evaluating a position of the deployed distal region relative to the native annulus. The clinician may further desire the ability to resheath or recapture the partially deployed region for subsequent repositioning of the prosthesis. Regardless, in the partially deployed state, the proximal region of the prosthetic heart valve must remain coupled to the delivery device. While, in theory, retaining a partially deployed prosthetic heart valve to the delivery device is straightforward, in actual practice the constraints presented by the stented prosthetic heart valve render the technique exceedingly difficult. In particular, the delivery device must not only securely retain the prosthetic heart valve in the partially deployed state, but also must consistently operate to release the prosthetic heart valve when full deployment is desired.

A stented heart valve is purposefully designed to rigidly resist collapsing forces once deployed so as to properly anchor itself in the anatomy of the heart. Thus, the delivery device component (e.g., outer delivery sheath) employed to retain the prosthesis in a collapsed arrangement must be capable of exerting a significant radial (inward) force. Conversely, this same delivery device component cannot be overly rigid so as to avoid damaging the transcatheter heart valve during deployment. Along these same lines, the aortic arch must be traversed with many percutaneous heart valve replacement procedures, necessitating that the delivery device provide sufficient articulation attributes. To meet these constraints, the outer delivery sheath typically incorporates a circumferentially rigid capsule, and a coupling structure is disposed within the delivery sheath for temporarily capturing the stented valve. While viable, conventional delivery device designs robustly engage the prosthetic heart valve within the capsule; this robust engagement facilitates the partial deployment technique described above, but the prosthetic heart valve may undesirably "catch" on the inner engagement structure when full deployment is intended and/or numerous, complex components are required to ensure complete deployment. Further, clinicians prefer that a significant portion of the prosthetic heart valve be exposed/expanded in the partially deployed state (e.g., the inflow region and at least a portion of the outflow region of the prosthesis). Unfortunately, existing delivery device designs cannot consistently meet this need.

In light of the above, a need exists for systems to restore (e.g., replace) a defective heart valve and corresponding stented transcatheter prosthetic heart valve delivery devices and methods that satisfy the constraints associated with percutaneous heart valve implantation and permit consistent partial and full deployment of the prosthesis.

SUMMARY

Some aspects in accordance with principles of the present disclosure relate to a delivery device for percutaneously deploying a stented prosthetic heart valve. The prosthetic heart valve has a stent frame to which a valve structure is attached. The delivery device includes a delivery sheath assembly, an inner shaft, and a capture assembly. The delivery sheath assembly terminates at a distal end and defines a lumen. The inner shaft is slidably disposed within the lumen. The capture assembly is configured to selectively couple the prosthetic heart valve relative to the inner shaft, and includes a spindle and at least one biasing member. The spindle is attached to the inner shaft and defines at least one longitudinal capture slot. The biasing member is disposed within the capture slot and is configured to self-transition from a deflected condition to a normal condition. In this regard, a radial projection of the biasing member relative to a centerline of the inner shaft is greater in the normal condition than in the deflected condition. With this in mind, the delivery device provides a delivery state in which the delivery sheath assembly retains a stented prosthetic heart valve over the inner shaft and coupled to the spindle via the capture slot, including a portion of the stented prosthetic heart valve being engaged within the capture slot and the biasing member forced to the deflected condition. The delivery device further provides a deployment state in which the distal end of the delivery sheath assembly is withdrawn from over the prosthetic heart valve and the capture slot to permit the prosthetic heart valve to release from the capture slot, including the biasing member self-transitioning toward the normal condition to exteriorly close at least a portion of the capture slot. In some embodiments, the spindle forms a plurality of circumferentially spaced capture slots, with the capture assembly further including a plurality of the biasing members, respective ones of which are disposed in corresponding ones of the capture slots. In yet other embodiments, the delivery device further includes a release sleeve assembly disposed between the delivery sheath assembly and the inner shaft, the release sleeve assembly including a release sleeve slidably received over at least a portion of the capture slot in the delivery state.

Yet other aspects in accordance with principles of the present disclosure relate to a system for restoring (e.g., replacing) a defective heart valve of a patient. The system includes a prosthetic heart valve and a delivery device. The prosthetic heart valve has a stent frame and a valve structure attached to the stent frame. Further, the stent frame includes a proximal region forming at least one post. The delivery device includes a delivery sheath assembly, an inner shaft, and a capture assembly. The delivery sheath assembly terminates at a distal end and defines a lumen. The inner shaft is slidably received within the lumen. The capture assembly includes a spindle attached to the inner shaft and at least one biasing member. The spindle forms at least one longitudinal capture slot sized to slidably receive the post of the stent frame. Further, the biasing member is disposed within the capture slot. The biasing member is configured to self-transition from a deflected condition to a normal condition, with a radial projection of the biasing member relative to a centerline of the inner shaft being greater in the normal condition than in the deflected condition. With this construction, the system is configured to provide a loaded mode in which the prosthetic heart valve is retained about the inner shaft by the delivery sheath assembly and the capture assembly, including the post being slidably engaged within the capture slot. In some embodiments, the proximal region of the stent frame forms a plurality of the posts, with the spindle forming a corresponding number of longitudinal capture slots. In related embodiments, a plurality of biasing members are provided, with each biasing member being disposed within a respective one of the capture slots. In other constructions, a deployment mode of the system includes the stent frame self-expanding from the delivery device, with the biasing member ejecting the post from the capture slot.

Yet other aspects in accordance with principles of the present disclosure relate to a method of percutaneously deploying a stented prosthetic heart valve to an implantation site of a patient. The method includes receiving a delivery device loaded with a radially expandable prosthetic heart valve having a stent frame to which a valve structure is attached. The delivery device includes a delivery sheath assembly containing the prosthetic heart valve in a compressed arrangement over an inner shaft in a delivery state of the device, as well as a capture assembly attached to the inner shaft. The capture assembly includes a spindle and at least one biasing member. The spindle forms at least one longitudinal capture slot within which the biasing member is disposed. The biasing member is configured to self-transition from a deflected condition to a normal condition, with a radial projection of the biasing member relative to a centerline of the inner shaft being greater in the normal condition than in the deflected condition. In the delivery state, the post forces the biasing member to the deflected condition. The prosthetic heart valve is delivered in the compressed arrangement through a bodily lumen of the patient to the implantation site via the delivery device in the delivery state. The delivery sheath assembly is proximally retracted from the prosthetic heart valve. The post is permitted to release from the capture slot, including the biasing member self-transitioning toward the normal condition to eject the post from the slot. In some embodiments, the delivery device further includes a release sleeve slidably received over the spindle in the delivery state to retain the post in the capture slot. With these embodiments, the method can further include proximally retracting the release sleeve relative to the capture slot to allow the biasing member to eject the post from the capture slot.

BRIEF DESCRIPTION OF THE DRAWINGS

FIG. 3 is an exploded, perspective view of a stented prosthetic heart valve delivery device in accordance with principles of the present disclosure;

FIG. 4B is a cross-sectional view of the capture assembly of FIG. 4A assembled to a portion of an inner shaft component of the delivery device of FIG. 3;

FIG. 4C is a cross-sectional view of the capture assembly of FIG. 4B, including a first biasing member component in a normal condition and a second biasing member in a deflected condition;

FIG. 7A is a cross-sectional view of a portion of a heart valve repair or replacement system in accordance with the present disclosure, including the delivery device of FIG. 3 loaded with the prosthetic heart valve of FIG. 1A;

FIGS. 9A and 9B are simplified perspective views of the delivery device of FIG. 3 in various stages of transitioning to a deployment state.

DETAILED DESCRIPTION

Figure 1A:
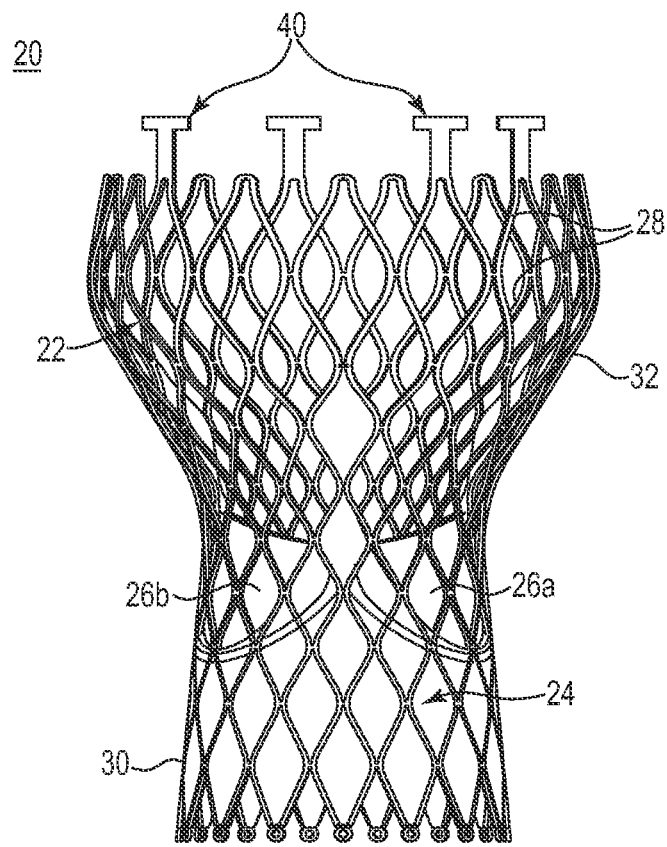
FIG. 1A is a side view of a stented prosthetic heart valve useful with systems, devices, and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached leaflets can be mounted onto a delivery device. The stent frame support structures are configured so that they can be changed to their normal, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
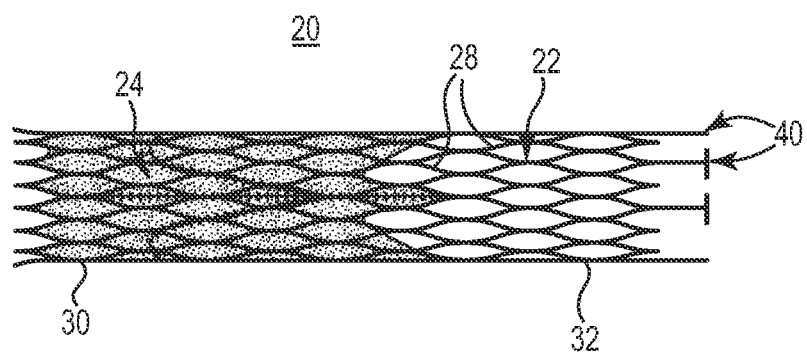
FIG. 1B is a side view of the prosthetic heart valve of FIG. 1A in a compressed arrangement.

With the above understanding in mind, one non-limiting example of a stented prosthetic heart valve 20 useful with systems and methods of the present disclosure is illustrated in FIG. 1A. As a point of reference, the prosthetic heart valve 20 is shown in a normal or expanded arrangement in the view of FIG. 1A; FIG. 1B illustrates the prosthetic heart valve 20 in a compressed arrangement (e.g., when compressively retained within an outer catheter or sheath (not shown)). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the normal, expanded arrangement (FIG. 1A). In other embodiments, the stent frame 22 is expandable to the expanded arrangement by a separate device (e.g., a balloon internally located within the stent frame 22). The valve structure 24 is assembled to the stent frame 22 and provides two or more (typically three) leaflets 26a, 26b. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for replacing an aortic valve. Alternatively, other shapes are also envisioned, adapted for the specific anatomy of the valve to be replaced (e.g., stented prosthetic heart valves in accordance with the present disclosure can alternatively be shaped and/or sized for replacing a native mitral, pulmonic, or tricuspid valve). Regardless, the valve structure 24 can be arranged to extend less than an entire length of the stent frame 22. In particular, the valve structure 24 can be assembled to, and extend along, an inflow region 30 of the prosthetic heart valve 20, whereas an outflow region 32 is free of the valve structure 24 material. The terms "inflow" and "outflow" are in reference to an arrangement of the prosthetic heart valve 20 upon final implantation relative to the native aortic valve (or other valve) being replaced A wide variety of other constructions are also acceptable and within the scope of the present disclosure. For example, the valve structure 24 can be sized and shaped to extend along an entirety, or a near entirety, of a length of the stent frame 22. With embodiments in which the prosthetic heart valve 20 is to be implanted via a retrograde approach, the prosthetic heart valve 20 will be arranged within the corresponding delivery device such that the inflow region 30 is distal the outflow region 32. Thus, the inflow region 30 can alternatively be referenced as the distal region of the prosthetic heart valve 20, whereas the outflow region 32 serves as the proximal region. With these conventions in mind, a proximal end 36 of the stent frame 22 forms, in some embodiments, a plurality of posts 40. The posts 40 are defined at an intersection of two (or more) adjacent ones of the wire segments 28, and are circumferentially spaced about a circumference defined by the stent frame 22. While the stent frame 22 is shown in FIGS. 1A and 1B as having four of the posts 40, any other number, either greater or lesser, is equally acceptable. For example, the stent frame 22 can include as few as a single one of the posts 40.

Figure 2:
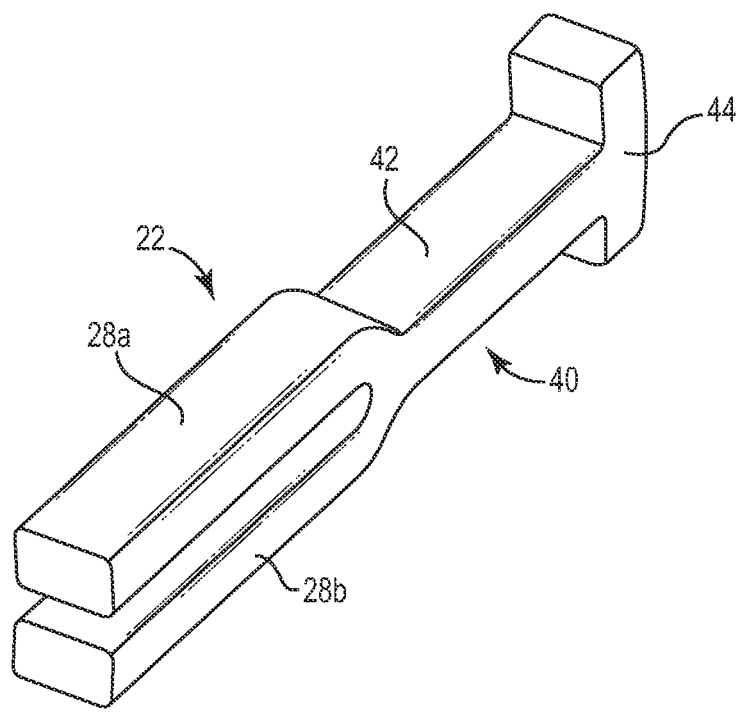
FIG. 2 is an enlarged, perspective view of a post portion of the prosthetic heart valve of FIGS. 1A and 1B.

The posts 40 can assume various forms, and in some embodiments are identical. FIG. 2 illustrates one construction of the post 40 contemplated by the present disclosure in greater detail. As a point of reference, in the view of FIG. 2, two of the wire segments 28a, 28b are illustrated as intersecting at the post 40, with the post 40 projecting proximally from the wire segments 28a, 28b; a remainder of the stent frame 22 is omitted from the view for ease of explanation. The post 40 includes a shoulder 42 and a head 44. With respect to an orientation of the post 40 relative to the circumference defined by the stent frame 22 (FIG. 1A), the shoulder 42 and the head 44 can be described as having or defining a circumferential width, with the circumferential width of the head 44 being greater than that of the shoulder 42 for reasons made clear below. With some constructions, then, the post 40 can have a T-like shape. A variety of other shapes are also acceptable. These and other features of the post 40, as well as the stent frame 22 as a whole, are described below in the context of loading to, and releasing from, a delivery device.

With the above understanding of the prosthetic heart valve 20 in mind, one embodiment of a transcatheter stented prosthetic heart valve delivery device 50 in accordance with principles of the present disclosure is shown in FIG. 3. The delivery device 50 includes a delivery sheath assembly 52, an inner shaft assembly 54, a capture assembly 56, and a handle 58. Other optional components, such as a release sleeve assembly 60, can also be included. Details on the various components are provided below. In general terms, however, the delivery device 50 combines with a stented prosthetic heart valve (not shown) to form a system for restoring (e.g., replacing) a defective heart valve of a patient. The delivery device 50 provides a delivery state in which the stented prosthetic heart valve is coupled to the inner shaft assembly 54 via the capture assembly 56, and compressively retained within a capsule 62 of the delivery sheath assembly 52. The delivery sheath assembly 52 can be manipulated to withdraw the capsule 62 proximally from the prosthetic heart valve via operation of the handle 58 in defining a deployment state of the delivery device 50, permitting the prosthesis to self-expand (alternatively, be caused to expand) and release from the inner shaft assembly 54 and the capture assembly 56. The optional release sleeve assembly 60, where provided, can operate to effectuate this release. Further, the handle 58 can be operated to maneuver the capsule 62 to effectuate a partial deployment state in which a distal region of the prosthetic heart valve is permitted to self-expand, whereas a proximal region of the prosthesis remains coupled to the capture assembly 56.

Various features of the components 52-60 reflected in FIG. 3 and described below can be modified or replaced with differing structures and/or mechanisms. Thus, the present disclosure is in no way limited to the delivery sheath assembly 52, the inner shaft assembly 54, the handle 58, etc., as shown and described below. For example, apart from the capture assembly 56, the delivery device 50 can have any of the constructions described in U.S. application Ser. No. 12/870,567 filed Aug. 27, 2010 entitled "Transcatheter Valve Delivery Systems and Methods" and Ser. No. 12/886,975 filed Sep. 21, 2010 and entitled "Stented Transcatheter Prosthetic Heart Valve Delivery System and Method"; the teachings of which are incorporated herein by reference. More generally, delivery devices in accordance with the present disclosure provide features capable of compressively retaining a self-deploying, stented prosthetic heart valve (e.g., the capsule 62 in combination with the capture assembly 56), and a mechanism capable of effectuating partial and full release or deployment of the prosthesis (e.g., retracting the capsule 62 alone or in combination with the optional release sheath assembly 60).

In some embodiments, the delivery sheath assembly 52 includes the capsule 62 and a shaft 70, and defines proximal and distal ends 72, 74. A lumen 76 (referenced generally) is formed by the delivery sheath assembly 52, extending from the distal end 74 through the capsule 62 and at least a portion of the shaft 70. The lumen 76 can be open at the proximal end 72. The capsule 62 extends distally from the shaft 70, and in some embodiments has a more stiffened construction (as compared to a stiffness of the shaft 70) that exhibits sufficient radial or circumferential rigidity to overtly resist the expected expansive forces of the stented prosthetic heart valve (not shown) when compressed within the capsule 62. For example, the shaft 70 can be a polymer tube embedded with a metal braiding, whereas the capsule 62 includes a laser-cut metal tube that is optionally embedded within a polymer covering. Alternatively, the capsule 62 and the shaft 70 can have a more uniform construction (e.g., a continuous polymer tube). Regardless, the capsule 62 is constructed to compressively retain the stented prosthetic heart valve at a predetermined diameter when loaded within the capsule 62, and the shaft 70 serves to connect the capsule 62 with the handle 58. The shaft 70 (as well as the capsule 62) is constructed to be sufficiently flexible for passage through a patient's vasculature, yet exhibits sufficient longitudinal rigidity to effectuate desired axial movement of the capsule 62. In other words, proximal retraction of the shaft 70 is directly transferred to the capsule 62 and causes a corresponding proximal retraction of the capsule 62. In other embodiments, the shaft 70 is further configured to transmit a user-generated rotational force or movement onto the capsule 62.

The inner shaft assembly 54 can have various constructions appropriate for supporting a stented prosthetic heart valve within the capsule 62. In some embodiments, the inner shaft assembly 54 include an inner support shaft 80 and a tip 82. The inner support shaft 80 is sized to be slidably received within the lumen 76 of the delivery sheath assembly 52, and is configured for mounting of the capture assembly 56 and the optional release sheath assembly 60. The inner support shaft 80 can include a distal segment 84 and a proximal segment 86. The distal segment 84 connects the tip 82 to the proximal segment 86, with the proximal segment 86, in turn, coupling the inner shaft assembly 54 to the handle 58. The components 80-86 can combine to define a continuous lumen 88 (referenced generally) sized to slidably receive an auxiliary component such as a guide wire (not shown).

The distal segment 84 can be a flexible polymer tube embedded with a metal braid. Other constructions are also acceptable so long as the distal segment 84 exhibits sufficient structural integrity to support a loaded, compressed stented prosthetic heart valve (not shown), as well as the capture assembly 56 and the optional release sheath assembly 60 mounted thereto. The proximal segment 86 can include, in some constructions, a leading portion 90 and a trailing portion 92. The leading portion 90 serves as a transition between the distal and proximal segments 84, 86, and thus in some embodiments is a flexible polymer tubing (e.g., PEEK) having an outer diameter slightly less than that of the distal segment 84. The trailing portion 92 has a more rigid construction (e.g., a metal hypotube), adapted for robust assembly with the handle 58. Other materials and constructions are also envisioned. For example, in alternative embodiments, the distal and proximal segments 84, 86 are integrally formed as a single, homogenous tube or solid shaft.

The tip 82 forms or defines a nose cone having a distally tapering outer surface adapted to promote atraumatic contact with bodily tissue. The tip 82 can be fixed or slidable relative to the inner support shaft 80.

The capture assembly 56 serves to selectively couple corresponding features of the stented prosthetic heart valve (not shown) relative to the inner shaft assembly 54, and can be configured for mounting to the inner support shaft 80. One embodiment of the capture assembly 56 is shown in greater detail in FIGS. 4A and 4B, and includes a spindle 100 and at least one biasing member 102.

The spindle 100 can assume various forms, and in some constructions includes a tubular base 104, a hub 106, and a flange 108. The hub 106 and the flange 108 radially project from the tubular base 104, with the spindle 100 forming one or more features configured to selectively engage the post(s) 40 (FIG. 2) of the stented prosthetic heart valve 20 (FIG. 1B) as described below.

The tubular base 104 is configured to facilitate mounting of the spindle 100 to the inner support shaft 80 (FIG. 3), and defines a central passageway or lumen 110, an intermediate section 112, and a proximal section 114. The intermediate section 112 is formed or defined between the hub 106 and the flange 108, and the proximal section 114 is formed or defined proximal the flange 108. As best shown in FIG. 4B, the proximal section 114 can be configured for attachment within the proximal segment 90 of the inner support shaft 80, for example by forming a stepped diameter shoulder 116. Other mounting techniques are also acceptable, such as the proximal section 114 being sized to coaxially receive the inner support shaft 80. Similarly, the lumen 110 can be sized to co-axially receive the distal segment 84 (FIG. 3) of the inner support shaft 80 for mounting thereto.

The hub 106 projects radially outwardly from the tubular base 104 to define an outer surface 120 and a trailing face 122 (best shown in FIG. 4B). The outer surface 120 includes or defines a rim 124 and a leading portion 126. The rim 124 defines a maximum diameter of the hub 106, with the leading portion 126 tapering in diameter in distal extension from the rim 124 to a leading face 128. In other embodiments, the leading portion 126 can have a more uniform diameter in extension from the rim 124. Regardless, the rim 124 is sized to slidably receive a separate sleeve-like component (e.g., a portion of the release sleeve assembly 60 (FIG. 3) as described below). In addition, the hub 106 forms or defines one or more longitudinally-extending capture slots 130. In some embodiments, a plurality of the longitudinal capture slots 130 are formed in the hub 106, commensurate with the number of the posts 40 (FIG. 1A) provided with the prosthetic heart valve 20 (FIG. 1A). The plurality of capture slots 130 can be identical and equidistantly spaced about a circumference of the hub 106. Alternatively, only a single one of the capture slots 130 need be provided. The capture slot(s) 130 extends through a radial thickness of the hub 106, and is exteriorly open at the outer surface 120 (e.g., the rim 124 and the leading portion 126) and the trailing face 122. A maximum height of the capture slot(s) 130 is defined at the rim 124 and is commensurate with (e.g., slightly greater than) a combined thickness of the stent frame post 40 (FIG. 2) and the biasing member 102 as described below. Further, a circumferential width of each of the capture slots 130 corresponds with a circumferential width of the post shoulder 42 (FIG. 2). Conversely, however, the circumferential width of each of the capture slots 130, at least at the trailing face 122, is less than the circumferential width of the post head 44 (FIG. 2). The various interior surfaces defining each of the capture slots 130 are relatively smooth to facilitate sliding of the post 40 relative thereto.

The flange 108 is proximally spaced from the hub 106, and radially projects from the tubular base 104. With this spacing, then, the intermediate section 112 of the tubular base 104 provides a reduced diameter cylindrical surface interposed between the hub 106 and the flange 108, with a diameter of the intermediate section 112 approximating, or longitudinally aligned with, a floor of each of the longitudinal capture slots 130. The outer diameter of the flange 108 can approximately the maximum outer diameter of the hub 106 (and in particular the rim 124) for reasons made clear below. Regardless, the larger diameter flange 108 combines with the larger diameter hub 106 and the intermediate section 112 to create a trough 134 configured to selectively receive the post head 44 (FIG. 2) as described below. Stated otherwise, the trough 134 is bounded by the trailing face 122 of the hub 106, the intermediate section 112 of the tubular base 104, and a distal face 136 of the flange 108. As best shown in FIG. 4B, the capture slot(s) 130 is open to the trough 134.

The flange 108 can form or define at least one longitudinally-extending clearance slot 140. In some embodiments, a plurality of the clearance slots 140 are formed, with the number and arrangement of the clearance slots 140 corresponding with the number and arrangement of the capture slots 130 in the hub 106 (e.g., respective ones of the clearance slots 140 are longitudinally aligned with corresponding ones of the capture slots 130). The clearance slots 140 in the flange 108 are open to the trough 134, and may or may not have a circumferential width commensurate with the circumferential width of the capture slots 130 in the hub 106. More generally, the clearance slots 140 in the flange 108 are sized and shaped to permit deflection of the biasing member(s) 102 as described below. In other embodiments, the flange 108 can be omitted.

While the spindle 100 has been described as forming the capture slots 130 to be discernable or separate from the clearance slots 140 (i.e., the capture slots 130 terminate at a side of the trough 134 opposite from a termination of the clearance slots 140), in other constructions, corresponding, longitudinally aligned ones of the slots 130, 140 can be defined as a single, continuous slot, with the hub 106 and the flange 108 essentially forming leading and trailing segments of the continuous slot, respectively. In yet other embodiments, the clearance slots 140 in the flange 108 can be omitted.

The spindle 100 can be integrally formed as a homogenous part in some embodiments. In other constructions, one or more of the hub 106 and/or the flange 108 can be separately manufactured and subsequently assembled to the tubular base 104. Alternatively, the hub 106 and/or the flange 108 can be directly mounted onto the inner support shaft 80. Regardless, the spindle 100 is constructed of a relatively rigid material able to maintain a structural integrity of the spindle 100 in supporting the prosthetic heart valve 20 (FIG. 1A) in the compressed arrangement.

Figure 4A:
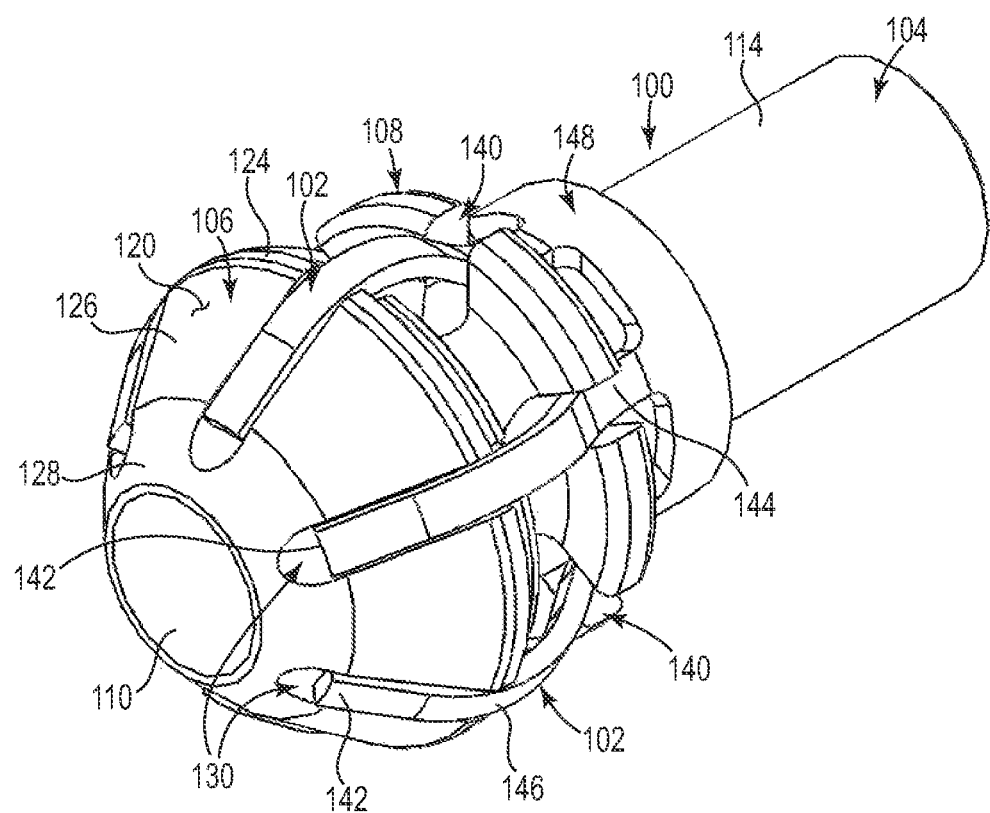
FIG. 4A is an enlarged, perspective view of a capture assembly portion of the delivery device of FIG. 3.

The biasing member 102 can be disposed within one of the capture slots 130 in the hub 106, and is configured to self-transition from a deflected condition to a normal condition (the normal condition of the biasing member 102 being reflected in FIGS. 4A and 4B). In some constructions, a plurality of the biasing members 102 are provided, with individual ones of the biasing members 102 being disposed within corresponding ones of the capture slots 130. In some embodiments, the biasing members 102 are leaf spring-like bodies, defining a free end 142, a fixed end 144, and an intermediate region 146. With this construction, the leaf spring biasing member 102 has a shape memory characteristic (e.g., the leaf spring biasing member 102 can be formed from a metal alloy (such as Nitinol™ or stainless steel), or a polymer having shape memory attributes) that imparts an outwardly curved shape to the intermediate region 146 in the natural condition of FIGS. 4A and 4B. Further, and as shown in FIG. 4C, the leaf spring biasing member 102, and in particular the intermediate region 146, can be deflected toward a more straightened shape (i.e., the deflected condition) via an externally applied force, and then self-revert or self-transition back to the normal condition upon removal of the external force. As a point of reference, FIG. 4C illustrates a comparison of the normal and deflected conditions of the biasing member 102, with a first biasing member 102a shown in the normal condition, and a second biasing member 102b shown in a deflected condition. Relative to a central axis C of the tubular base 104 (and thus of the inner support shaft 80), a radially-outward projection of the biasing member 102 in the normal condition is greater than the radial projection in the deflected condition. In other words, relative to the central axis C, the intermediate region 146 of the biasing member 102a in the normal condition extends radially beyond a radial extension of the intermediate region 146 of the biasing member 102b in the deflected condition.

The leaf spring biasing member 102 is sized for placement and deflection within a corresponding one of the capture slots 130. Thus, a width of at least the intermediate region 146 corresponds with (e.g., is slightly less than) a circumferential width of the corresponding capture slot 130. Further, a shape of the intermediate region 146 in the normal condition is such that upon assembly of the fixed end 144 to the tubular base 104, the intermediate region 146 is approximately radially aligned with the rim 124. In some constructions, upon final assembly, the biasing member 102 is configured and arranged such that the intermediate region 146 projects slightly radially above the rim 124 in the normal condition. With other embodiments in which the normal condition of the biasing member 102 positions the intermediate region 146 slightly below the rim 124, a radial distance between the intermediate region 146 and the rim 124 is less than a thickness of the stent post 40 (FIG. 2) for reasons made clear below. Regardless, in the normal condition, the biasing member 102 substantially exteriorly closes the corresponding capture slot 130 at least at the rim 124. In related embodiments, the intermediate region 146 extends along at least a majority of a longitudinal length of the corresponding capture slot 130 and approximates a contour of the outer surface 120 at the leading portion 126 so as to exteriorly close at least a majority of the capture slot 130 relative to the outer surface 120 in the normal condition. [53] Assembly of the biasing member(s) 102 to the spindle 100 can assume various forms. For example, in one embodiment in which a plurality of the biasing members 102 are provided, a ring 148 can be formed that interconnects the fixed end 144 of each of the biasing members 102. The ring 148 is then mounted to the proximal section 114 of the tubular base 104 (e.g., adhesive, welding, etc.). With this but one acceptable construction, then, each of the biasing members 102 longitudinally projects through a corresponding one of the clearance slots 140 in the flange 108, across the trough 134, and into the corresponding one of the capture slots 130. The free end 142 of each of the biasing members 102 is not directly attached to the spindle 100. Thus, in transitioning from the deflected condition to the normal condition, the free end 142 moves proximally. Alternatively, the ring 148 can be omitted and the fixed end(s) 144 directly attached to the spindle 100. Further, while the fixed end 144 has been described as being arranged proximal the flange 108, in other constructions, the fixed end 144 is attached to the spindle 100 within or distal the corresponding capture slot 130 such that the free end 142 is proximal the fixed end 144.

While the biasing members 102 have been described as being leaf spring-like bodies, other constructions are also acceptable. For example, the biasing members 102 can be helical springs, linkages, elastically deformable bodies, etc., capable of exteriorly closing at least a portion of the corresponding capture slot 130 and ejecting the stent post 40 (FIG. 2) from engagement within the capture slot 130 in self-transitioning from a deflected condition to a normal condition (otherwise having an increased radial projection relative to the central axis C of the inner support shaft 80).

Returning to FIG. 3, the optional release sleeve assembly 60 is generally constructed to selectively capture the prosthetic heart valve 20 (FIG. 1A) to the capture assembly 56, and in particular the spindle 100. With this in mind, the release sleeve assembly 60 includes a mounting collar 150, one or more biasing arms 152, and a release sleeve 154. In general terms, the mounting collar 150 associates the release sleeve assembly 60 with the inner support shaft 80. The release sleeve 154 is sized to be slidably disposed over the spindle 100, with the biasing arms 152 serving to bias the release sleeve 154 to a longitudinal position relative to the mounting collar 150, and thus relative to the spindle 100, as described below.

The mounting collar 150 can assume various configurations appropriate for non-moveable, fixed mounting to (or relative to) the inner support shaft 80. For example, the mounting collar 150 can be a ring that is bonded to the inner support shaft 80. Other structures appropriate for establishing a fixed location relative to the inner support shaft 80 as well as resisting forces generated in or by the biasing arm(s) 152 are also envisioned. For example, in other embodiments, the mounting collar 150 can be omitted and an end of each of the biasing arm(s) 152 opposite the release sleeve 154 directly attached to the inner support shaft 80. Alternatively, the mounting collar 150 and/or the biasing arm(s) 152 can be affixed to the spindle 100 (that in turn is attached to the inner support shaft 80).

The biasing arms 152 are leaf spring-like bodies, and are spaced from one another about a periphery of the release sleeve 154. In some constructions, the release sleeve assembly 60 will include at least two of the biasing arms 152, which may be positioned at generally opposite sides of the release sleeve 154, if desired, although it is possible that they are positioned differently relative to each other. In other constructions, only one of the biasing arms 152 is provided. In yet other embodiments, the release sleeve assembly 60 includes three or more biasing arm 152, and each of the biasing arms 152 may be configured the same or differently than the other biasing arms 152. Regardless, and as described in greater detail below, the biasing arm(s) 152 can have a shape memory attribute, normally or naturally assuming the outwardly curved shape reflected in FIG. 3, and can be externally forced to deflect to a more straightened shape. Upon removal of the external force, the biasing arm(s) 152 self-revert back toward the normal curved shape. Other spring-related shapes or structures are also acceptable.

Figure 5:
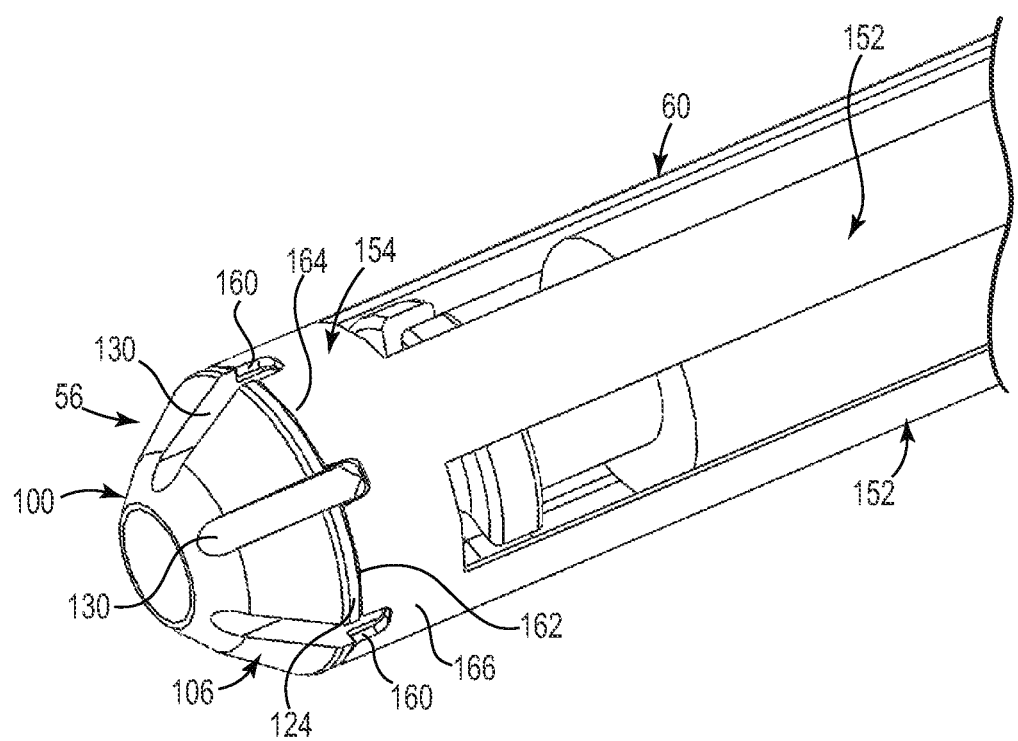
FIG. 5 is a perspective view of a portion of a release sheath assembly component of the delivery device of FIG. 3 and assembled over the capture assembly of FIG. 4A.

The release sleeve 154 is a tubular body sized to be slidably received over the spindle 100, and in particular the flange 108 and the rim 124 of the hub 106. The release sleeve 154 is designed to move freely over the flange 108 and the rim 124 due to a gap clearance (e.g., on the order of 0.001 inch or greater) that is provided between the release sleeve 154 and the maximum outer diameter of the flange 108 and the rim 124. In some constructions, and as best shown in FIG. 5 (that otherwise illustrates the release sleeve 154 assembled over the flange 108 (hidden in FIG. 5 but shown in FIG. 4A) and the rim 124, the biasing members 102 being omitted from the view of FIG. 5 for ease of explanation), the release sleeve 154 forms or defines at least one longitudinal notch 160 extending from, and open relative to, a distal end 162 thereof. The release sleeve 154 can include or form a plurality of the notches 160 corresponding with the number of the capture slots 130 provided with the hub 106. The notches 160 can be identical and are arranged relative to a circumference of the release sleeve 154 such that each of the notches 160 is longitudinally aligned with a corresponding one of the capture slots 130 upon assembly of the release sleeve 154 over the spindle 100. With embodiments in which the release sleeve 154 forms two (or more) of the notches 160, two (or more) fingers 164 are formed by or between adjacent ones of the notches 160. Regardless, a capture segment 166 is formed by the release sleeve 154 having a continuous, uninterrupted circumference. Thus, in other embodiments, the notches 160 can be omitted.

Returning to FIG. 3, the release sleeve assembly 60, including the biasing arms 152 and/or the release sleeve 154, can be made of one of more materials such as metal or polymers (e.g., Nitinol™, stainless steel, Delrin™, and the like). The material(s) have a thickness on the order of 0.002-0.007 inch, for example, although the thickness can be lower or higher than this size range. The release sleeve assembly 60 can have a length on the order of 5-15 mm, for example, in order to provide both flexibility and spring-radial strength to the components. The material(s) can have either a closed cell or an open-cell design.

Figure 6A:
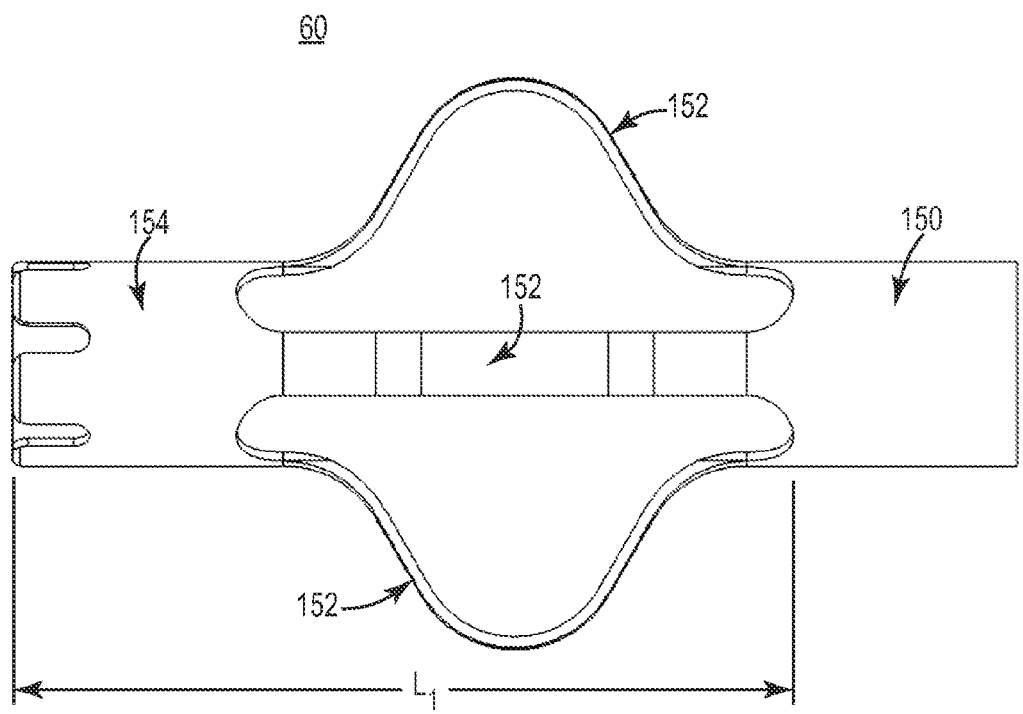
FIG. 6A is a simplified, side view of the release sheath assembly component of the delivery device of FIG. 3 and in a normal condition.
Figure 6B:
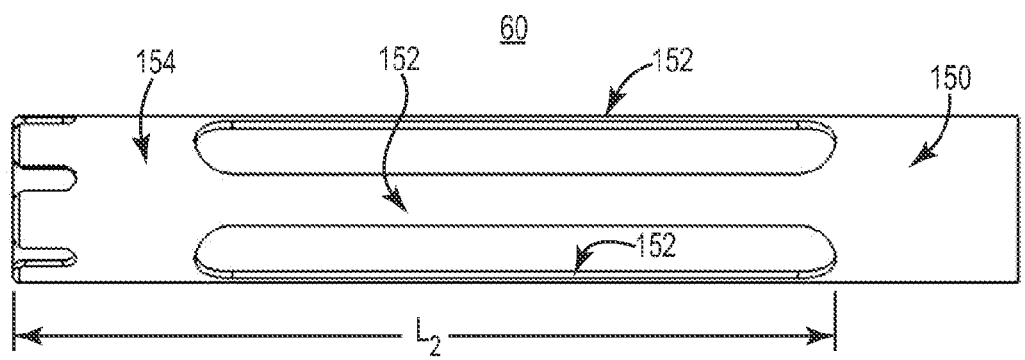
FIG. 6B is a simplified view of the release sheath assembly of FIG. 6A and in a compressed condition.

Operation of the release sleeve assembly 60 in facilitating partial and full deployment of a prosthetic heart valve is based upon a longitudinal position of the release sleeve 154 as dictated by biasing arms 152. As mentioned above, the biasing arms 152 are formed to normally assume the curved shape generally reflected in FIG. 3. A diameter collectively defined by the biasing arms 152 (in their normal state) is greater than a diameter of the delivery sheath assembly lumen 76. Thus, when the release sleeve assembly 60 is disposed within the capsule 62 (or within the delivery sheath shaft 70), the biasing arms 152 are forced to deflect radially inwardly, effectuating an increase in a longitudinal spacing between the collar 150 and the release sleeve 154. Upon removal of this external force, the biasing arms 152 self-revert back to the natural condition reflected in FIG. 3, thereby biasing the release sleeve 154 to an original longitudinal spacing relative to the collar 150. FIGS. 6A and 6B illustrate this relationship in simplified form. FIG. 6A reflects a normal state of the biasing arms 152 that establishes a first longitudinal spacing $L_1$ between the collar 150 and the release sleeve 154. When subjected to a compressive force (e.g., upon insertion within the delivery sheath assembly 52 (FIG. 3)), the biasing arms 152 deflect inwardly as shown in FIG. 6B. Because the collar 150 is spatially fixed (e.g., attached to the inner support shaft 80 (FIG. 3)), the deflected biasing arms 152 force the release sleeve 154 away from the collar 150, to a second longitudinal spacing $L_2$ that is greater than the first longitudinal spacing $L_1$. When the compressive force is removed, the biasing arms 152 self-revert back to the arrangement of FIG. 6A, thereby pulling the release sleeve 154 back toward the collar 150.

Returning the FIG. 3, the handle 58 generally includes a housing 170 and an actuator mechanism 172 (referenced generally). The housing 170 maintains the actuator mechanism 172, with the actuator mechanism 172 configured to facilitate sliding movement of the delivery sheath assembly 52 relative to the inner shaft assembly 54. The housing 170 can have any shape or size appropriate for convenient handling by a user. In one simplified construction, the actuator mechanism 172 includes a user interface or actuator 174 slidably retained by the housing 170 and coupled to a sheath connector body 176. The proximal end 72 of the delivery sheath assembly 52 is coupled to the sheath connector body 176 (e.g., via an optional mounting boss 178 in some embodiments). The inner shaft assembly 54, and in particular the proximal tube 86, is slidably received within a passage 180 of the sheath connector body 176, and is rigidly coupled to the housing 170. Sliding of the actuator 174 relative to the housing 170 thus causes the delivery sheath assembly 52 to move or slide relative to the inner shaft assembly 54 and the capture assembly 56, for example to effectuate deployment of a prosthesis from the inner shaft assembly 54 as described below. Alternatively, the actuator mechanism 172 can assume a variety of other forms differing from those implicated by the illustration of FIG. 3. Similarly, the handle 58 can incorporate other features, such as a cap 182 and/or a fluid port assembly 184.

FIG. 7A illustrates a portion of a system 200 in accordance with the present disclosure for restoring (e.g., replacing or repairing) a defective heart valve of a patient and including the stented prosthetic heart valve 20 loaded within the delivery device 50. As used throughout this specification, "repair" of a defective heart valve is inclusive of implanting a replacement prosthetic heart valve to or over a native valve, as well as alternatively maintaining the native leaflets in tact and functional. In the delivery state of the delivery device 50 in FIG. 7A, the prosthetic heart valve 20 is crimped over the inner shaft assembly 54, with the delivery sheath assembly 52 located to surround and compressively retain the prosthetic heart valve 20 in the compressed arrangement shown, thereby defining a loaded mode of the system 200. The capture assembly 56 and the release sleeve assembly 60 (referenced generally) are mounted to the inner support shaft 80, with the release sleeve 154 being distally forward to capture the posts 40 of the prosthetic heart valve 20 with the capture assembly 56. More particularly, the release sleeve 154 bears against each of the posts 40, in turn imparting a compressive force onto each of the biasing members 102, thereby forcing the biasing members 102 to the deflected condition.

Figure 7B:
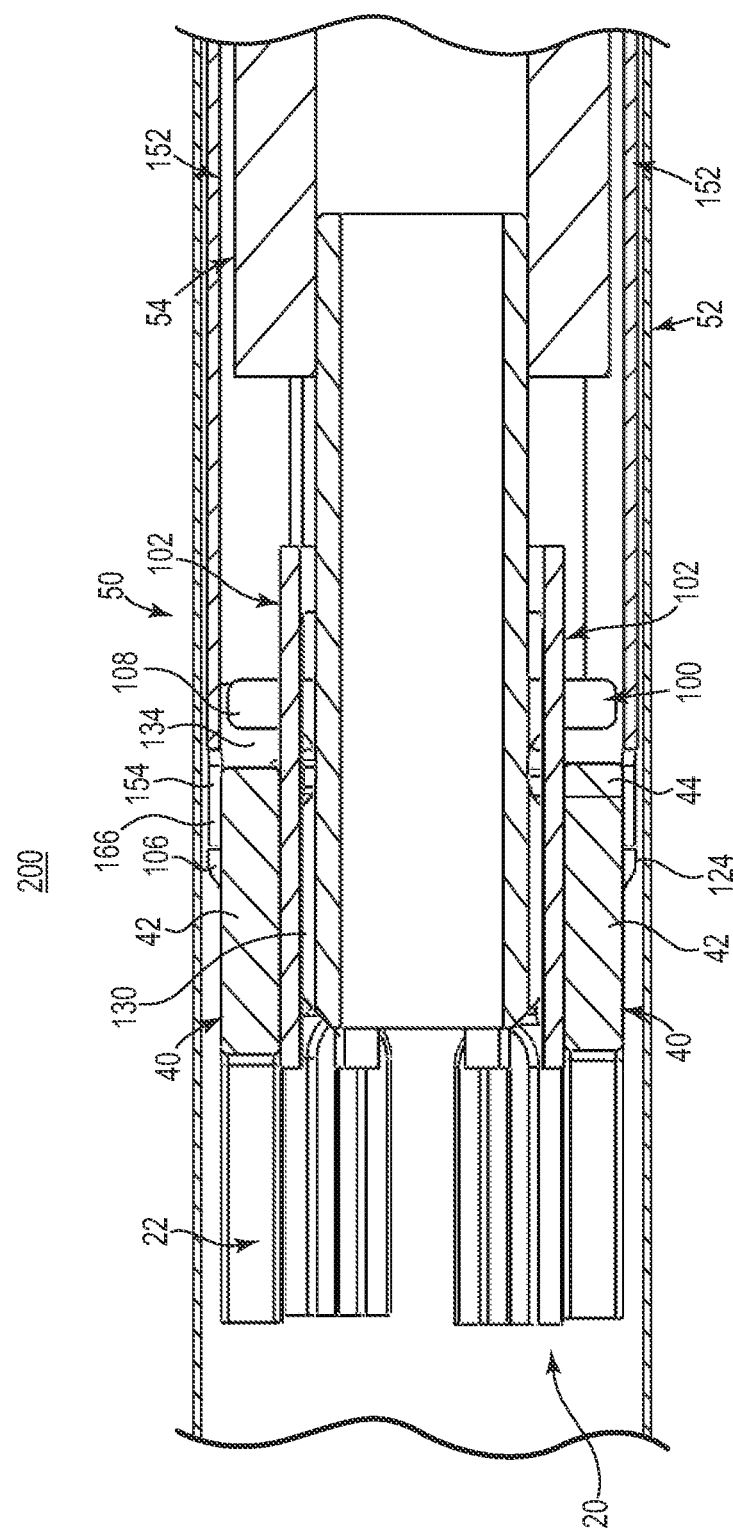
FIG. 7B is an enlarged cross-sectional view of a portion of the system of FIG. 7A.

Engagement of the prosthetic heart valve 20 with the capture assembly 56 is more fully illustrated in FIG. 7B. As a point of reference, FIG. 7B illustrate a portion of the system 200 in the loaded mode, including a portion of the delivery device 50 in the delivery state along with a portion of the prosthetic heart valve 20. For ease of explanation, portions of the inner shaft assembly 54 distal the spindle 100 is omitted from the view of FIG. 7B. In the delivery state, the delivery sheath assembly 52 acts upon the biasing arms 152 in turn causing the release sleeve 154 to slide distally over the flange 108 and a portion of the hub 106 (partially hidden in FIG. 7B). Each of the posts 40 is slidably engaged within a respective one of the capture slots 130. In the loaded mode of FIG. 7B, the shoulder 42 of the post 40 slidably nests within the capture slot 130 (referenced generally), and the head 44 nests within the trough 134. Further, due to compression of the prosthetic heart valve 20 to the compressed arrangement and/or the compressive force exerted by the release sleeve 154 onto the post 40, the corresponding biasing member 102 is forced to the deflected condition as shown. Thus, the biasing member 102 does not exteriorly close the capture slot 130 in the deflected condition. A radial height of each of the capture slots 130 is less than a combined thickness of the corresponding biasing member 102 and post 40 such that in the loaded mode (and deflected condition of the biasing member 102), the post 40 does not project radially beyond the capture slot 130 or the trough 134. It will be recalled that in some constructions, the stent frame 22 is configured to self-expand from the compressed arrangement reflected by FIG. 7B. Further, the biasing member 102 exerts a radial outward force onto the corresponding post 40. While the capsule 62 (FIG. 3) serves to resist this expansion, the release sleeve 154 further ensures robust retention of the post 40 with the spindle 100. In particular, the sleeve segment 166 extends to (or optionally over) the trough 134 and thus over the head 44. As a result, the head 44 is effectively captured within the trough 134 by the release sleeve 154. Further, the release sleeve 154 extends over the rim 124 (FIG. 4A) and thus over at least a portion of the capture slots 130, serving to further retain the posts 40 within the respective capture slots 130.

The loaded system 200 can then be used to percutaneously deliver the prosthetic heart valve 20 to an implantation site, such as a defective heart valve. For example, the delivery device 50 is manipulated to advance the compressed prosthetic heart valve 20 toward the implantation site in a retrograde manner through a cut-down to the femoral artery, into the patient's descending aorta, over the aortic arch, through the ascending aorta, and approximately midway across the defective aortic valve (for an aortic valve repair procedure). The prosthetic heart valve 20 can then be partially or fully deployed from the delivery device 50. With either procedure, the capsule 62 (FIG. 3) is proximally retracted or withdrawn from over the prosthetic heart valve 20. As generally reflected in FIG. 8A, proximal retraction of the capsule 62 continues, with the distal end 74 being approximately over the hub 106. Because the biasing arms 152 (FIG. 3) are still within the capsule 62 in the arrangement of FIG. 8A, the release sleeve 154 remains in the distally forward position relative to the hub 106. For ease of illustration, the prosthetic heart valve 20 is not shown in the view of FIG. 8A. However, FIG. 8B illustrates, in simplified form, partial retraction of the capsule 62 and the resultant self-expansion of an exposed, distal region 210 of the prosthetic heart valve 20 relative to the distal end 74 of the capsule 62.

Figure 8A:
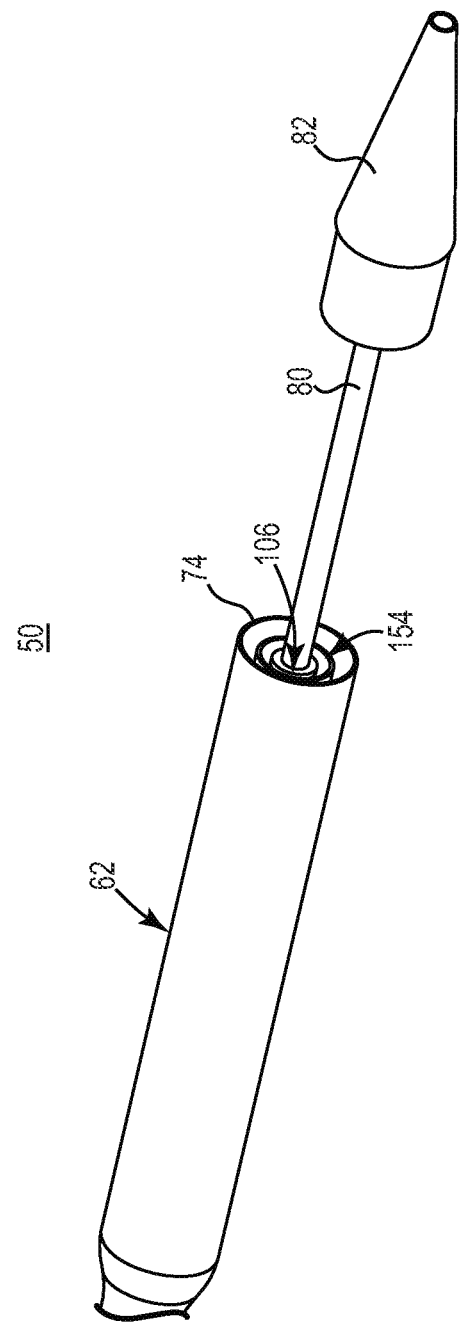
FIG. 8A is a perspective view of the delivery device of FIG. 3 in an initial stage of a partial deployment state.
Figure 8B:
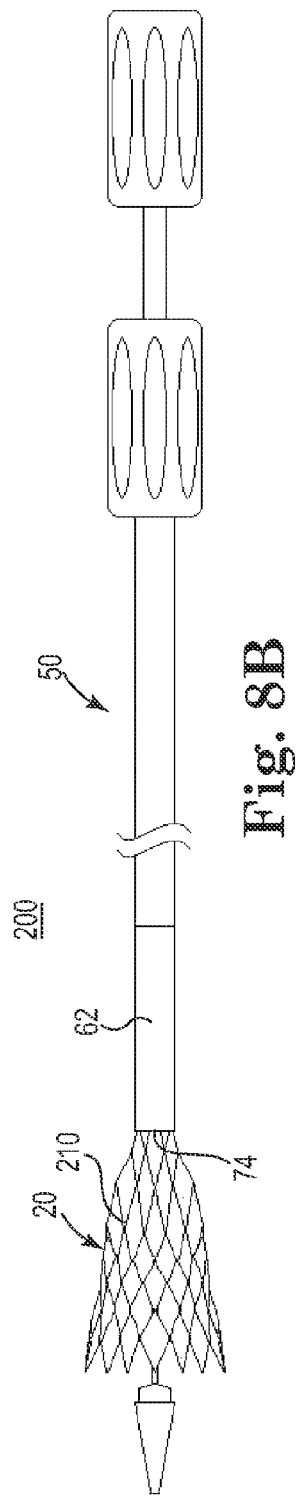
FIG. 8B is a simplified side view of the system of FIG. 7A in an initial stage of a deployment condition, including the delivery device in the arrangement of FIG. 8A.

With cross-reference between FIGS. 7B and 8A, so long as the distal end 74 of the capsule 62 is distal the biasing arms 152, the biasing arms 152 remain in a deflected condition such that the release sleeve 154 remains over the trough 134 and at least a portion of the capture slots 130. Thus, the shoulder 42 of each of the posts 40 remains engaged within the corresponding capture slot 130 as described above, as does the head 44 within the trough 134. As a result, in the stage of the partial deployment mode of FIG. 8A, the prosthetic heart valve 20 is able to partially expand or deploy, yet remains coupled to the delivery device 50 via the capture assembly 56 and the release sleeve 154.

Figure 8C:
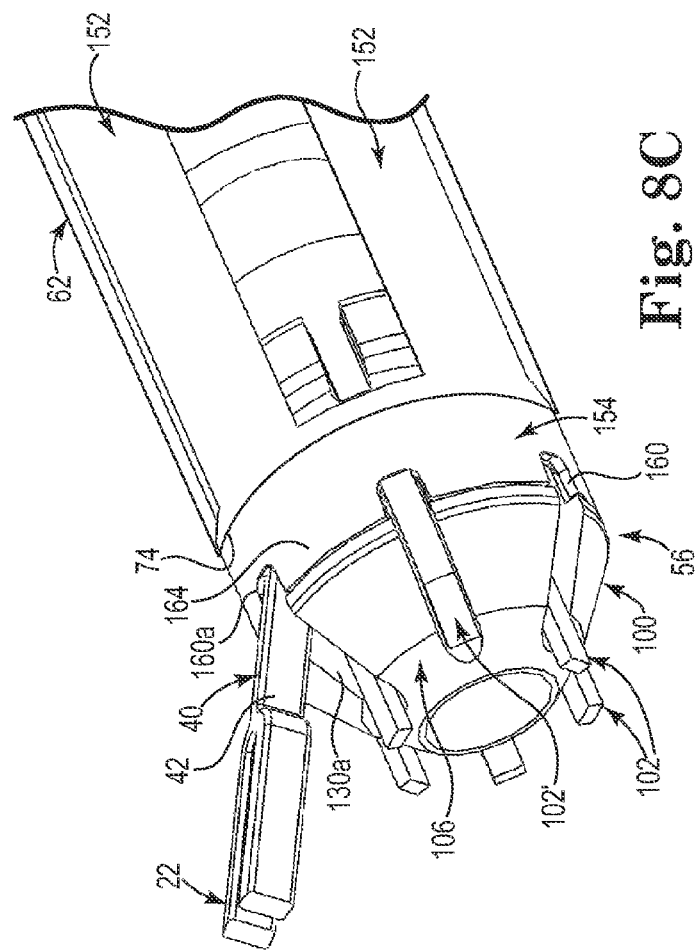
FIG. 8C is an enlarged, perspective view of the system of FIG. 7A in a further stage of the partial deployment state.

Partial deployment of the prosthetic heart valve 20 can also include further sequential retraction of the capsule 62 from the position of FIG. 8A. For example, in the partial deployment stage reflected by FIG. 8C (in which portions of the inner shaft assembly 54 distal the spindle 100 are omitted for ease of illustration), the distal end 74 of the capsule 62 (drawn in phantom) is further retracted relative to the hub 106 (as compared to the stage of FIG. 8A), with the distal end 74 located proximal the notches 160. However, because the biasing arms 152 are still within, thus acted upon by, the capsule 62, the release sleeve 154 remains over the trough 134 (hidden in FIG. 8C) such that the stent frame 22 remains coupled to the capture assembly 56 (via the posts 40). For ease of illustration, FIG. 8C illustrates a single one of the posts 40; five of the biasing members 102 are shown in the deflected condition described above, a sixth one of the biasing members 102' is illustrated in the normal condition for purposes of comparison. With embodiments in which the release sleeve 154 forms the notches 160, FIG. 8C further reflects that in this stage of the partial deployment mode, the stent frame posts 40 can pivot relative to the spindle 100. More particularly, with respect to the first capture slot 130a within which the post 40 of FIG. 8C is disposed, the corresponding first notch 160a of the release sleeve 154 is longitudinally aligned with the first capture slot 130a. Thus, with the distal end 74 of the capsule 62 proximal the first notch 160a, the self-expanding attribute of the stent frame 22 causes the shoulder 42 of the post 40 to slide through the first capture slot 130a and the first notch 160a, with the head 44 (hidden in FIG. 8C) effectively pivoting within the trough 134 (hidden in FIG. 8C). Even with this pivoting movement, however, the head 44 remains captured within the trough 134 via the fingers 164.

In the stage of partial deployment of FIG. 8C (or in any other sequentially prior stage of partial deployment), the clinician can perform desired evaluations of the partially deployed prosthetic heart valve 20 (FIG. 8B) relative to the implantation site. Notably, a substantial majority of the prosthetic heart valve 20 is in an expanded arrangement, including, for example, the inflow region 30 (FIG. 1A) and at least a portion of the outflow region 32 (FIG. 1A). Thus, the systems and delivery devices and methods of the present disclosure afford the clinician the ability to make an accurate estimate of the position of the prosthetic heart valve 20 relative to the implantation site. Under circumstances where the clinician determines that the prosthetic heart valve 20 should be repositioned, the capsule 62 can, in some constructions, be distally advanced back over the prosthetic heart valve 20, thereby resheathing or recapturing the prosthetic heart valve 20 and returning to the compressed arrangement. Alternatively, the delivery device 50 can incorporate other features to effectuate recapturing of the prosthetic heart valve 20.

Figure 9A:
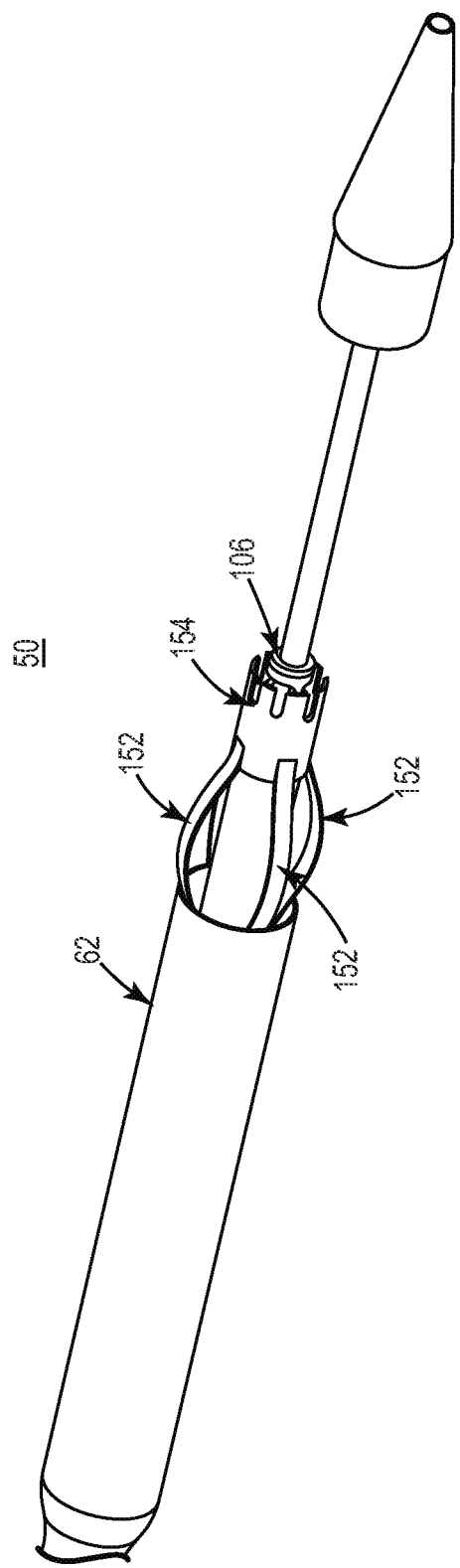

When full deployment of the prosthetic heart valve 20 from the delivery device 50 is desired, the capsule 62 is further proximally retracted over the biasing arms 152. As shown in FIGS. 9A and 9B (the prosthesis 20 (FIG. 1A) being omitted from the views of FIGS. 9A and 9B for ease of explanation), as the biasing arms 152 are sequentially released from the confines of the capsule 62, the biasing arms 152 self-revert toward their natural state. This action, in turn, proximally retracts the release sleeve 154 from the hub 106 and the trough 134 as reflected by a comparison of the arrangement of FIG. 9A with that of FIG. 9B. For ease of illustration, the biasing members 102 (FIG. 4A) are omitted from the views of FIGS. 9A and 9B.

Figure 10:
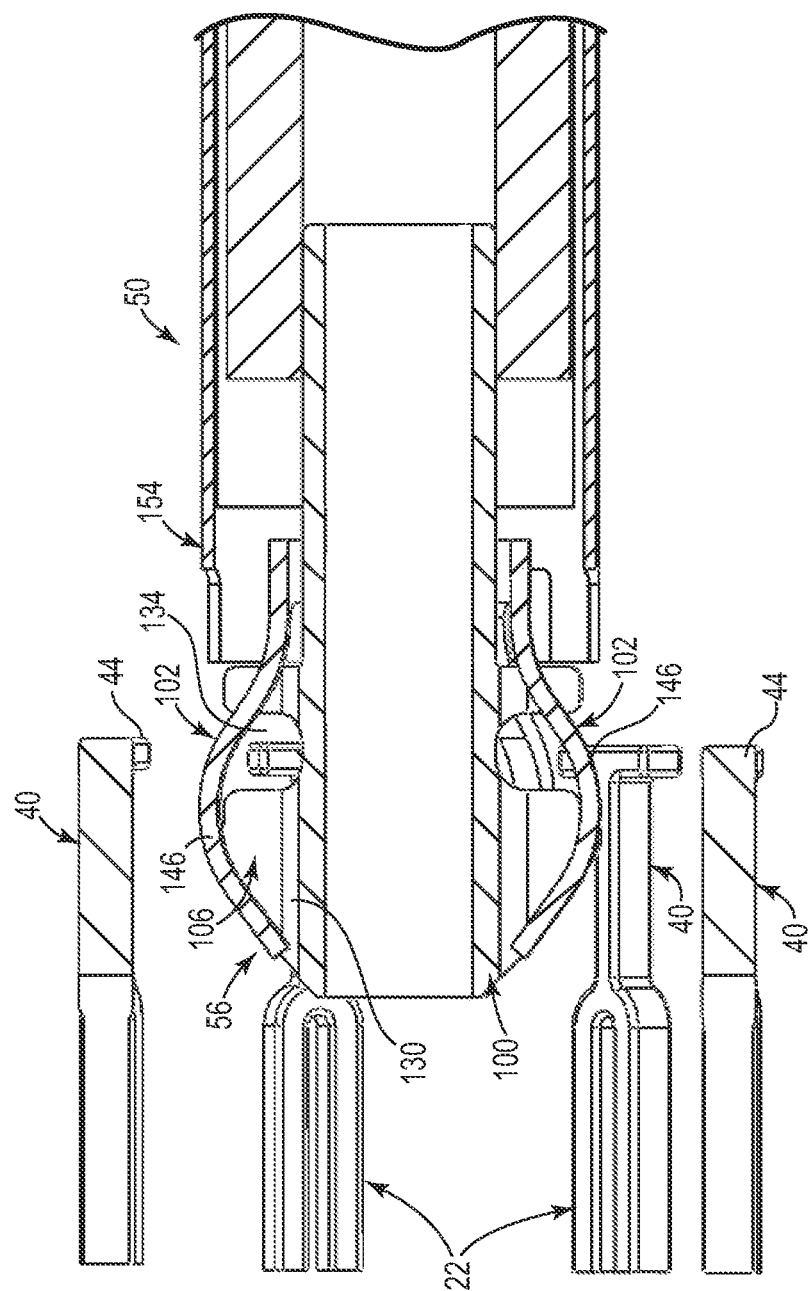
FIG. 10 is an enlarged, cross-sectional view of a portion of the system of FIG. 7A and illustrating transitioning to a deployment condition in which the prosthetic heart valve deploys from the delivery device.

Retraction of the release sleeve 154 from the hub 106 and the trough 134 permits the stent posts 40 to fully release from the capture assembly 56 as shown in FIG. 10. For example, in the view of FIG. 10, the release sleeve 154 has fully retracted from the hub 106 and the trough 134. Thus, the head 44 of each of the stent posts 40 is no longer captured by the release sleeve 154, and thus can fully release from the spindle 100 due, for example, to self-expansion of the prosthetic heart valve stent frame 22. In this regard, the biasing members 102 can now freely self-transition to the normal condition shown, completely ejecting the stent posts 40 from the corresponding capture slots 130 (referenced generally) and the trough 134. As shown, in the normal condition, the intermediate region 146 of each of the biasing members 102 is radially aligned with, or projects radially beyond, the outer surface 120 of the hub 106, thereby exteriorly closing at least a portion of the corresponding capture slot 130 and ensuring that the posts 40 are fully ejected from the capture slots 130 and the trough 134. Effectively then, the biasing members 102, in their normal condition, the prevent the stent frame 22 from catching on the spindle 100 when releasing or deploying from the delivery device 50. Thus, the posts 40 consistently release from the spindle 100.

While the delivery device 50 has been described as incorporating the release sleeve assembly 60, in other embodiments, the release sleeve assembly can have differing forms or can be omitted. For example, alternative delivery device configurations capture the prosthetic heart valve stent frame 22 relative to the spindle 100 via the delivery sheath assembly 52 (FIG. 3) alone. With these constructions, full deployment of the prosthetic heart valve 20 is effectuated once the distal end 74 (FIG. 3) of the capsule 62 (FIG. 3) is proximal the trough 134.

The delivery devices of the present disclosure provide percutaneous placement of a stented prosthetic heart valve for replacement of an aortic valve, for example. Alternatively, the systems and devices can be used for replacement or repair of other valves and/or in other portions of the body in which a stent is to be implanted. When delivering a valved stent to replace an aortic valve, the delivery devices of the present disclosure can be used with a retrograde delivery approach, for example, although it is contemplated that an antegrade delivery approach can be used, with certain modifications to the delivery device. With the repair systems described herein, full or partial blood flow through the native valve can advantageously be maintained during a period when the valved stent is being deployed into the patient, but is not yet released from its delivery device. This feature can help to prevent complications that may occur when blood flow is stopped or blocked during valve implantation with some other known delivery devices. In addition, it is possible for the clinician to thereby evaluate the opening and closing of leaflets, examine for any paravalvular leakage, and evaluate coronary flow and proper positioning of the prosthetic heart valve within the target anatomy before final release of the stented prosthesis.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices will further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthesis to an expanded arrangement.

The systems, devices, and methods of the present disclosure provide a marked improvement over previous designs. The delivery device is configured so that the stent frame of the stented prosthetic heart valve will release from the delivery device at a pre-designated step of the delivery sequence. These delivery devices thereby advantageously allow the clinician to entirely remove an outer sheath from a valved stent prior to releasing the stent from the delivery device. In addition, the systems of the present disclosure allow the inflow region and at least a portion of the outflow region of the valved stent to open or release so that the valve structure function can be determined prior to final release of the stented valve. The disclosed capture assembly provides a simplified design that better ensures consistent deployment, as well as promotes use with optional T-like shaped posts of the prosthetic heart valve stent frame to permit open assessment prior to full deployment.

Although the present disclosure has been described with reference to preferred embodiments, workers skilled in the art will recognize that changes can be made in form and detail without departing from the spirit and scope of the present disclosure.

What is claimed is:

1. A delivery device for percutaneously deploying a stented prosthetic heart valve including a stent frame to which a valve structure is attached, the device comprising:
 a delivery sheath assembly terminating at a distal end and defining a lumen;
 an inner shaft slidably disposed within the lumen; and
 a capture assembly for selectively coupling a prosthetic heart valve relative to the inner shaft, the capture assembly including:
 a spindle attached to the inner shaft, the spindle defining a plurality of circumferentially spaced capture slots,
 a first biasing member disposed within a first one of the plurality of capture slots and configured to self-transition from a deflected condition to a normal condition, wherein a radial projection of the biasing member relative to a centerline of the inner shaft is greater in the normal condition than in the deflected condition;

wherein the delivery device is configured to provide:

a delivery state in which the delivery sheath assembly is configured to retain a stented prosthetic heart valve over the inner shaft via the first capture slot, including a portion of the prosthetic heart valve engageable within the first capture slot and the first biasing member forced to the deflected condition, a deployment state in which the distal end of the delivery sheath assembly is withdrawn from the first capture slot, including the first biasing member self-transitioning toward the normal condition to exteriorly close at least a portion of the first capture slot.

2. The delivery device of claim 1, wherein the first biasing member is one of a plurality of biasing members, respective ones of the plurality of biasing members being disposed within respective ones of the capture slots.

3. The delivery device of claim 1, wherein the spindle includes a distal hub and a proximal flange, the hub and the flange being longitudinally spaced from one another to define a circumferential trough.

4. The delivery device of claim 3, wherein the first capture slot is formed in the hub and is open to the trough.

5. The delivery device of claim 4, wherein the flange forms a longitudinal clearance slot that is longitudinally aligned with the first capture slot.

6. The delivery device of claim 4, wherein the first biasing member extends across the trough.

7. The delivery device of claim 4, wherein the first biasing member extends through at least a majority of the first capture slot in the normal condition.

8. The delivery device of claim 7, wherein at least a portion of the first biasing member projects radially beyond an outer surface of the hub in the normal condition.

9. The delivery device of claim 1, wherein the first biasing member is a leaf spring body defining a free end, a fixed end, and an intermediate region, the intermediate region having a shape memory curve shape in the normal condition.

10. The delivery device of claim 9, wherein the fixed end is spatially affixed relative to the spindle.

11. The delivery device of claim 10, wherein the first biasing member is one of a plurality of biasing members, the fixed end of each of the biasing members being connected to a collar, and further wherein the collar is attached to the spindle.

12. The delivery device of claim 10, wherein the first biasing member is configured such that self-transitioning from the deflected condition to the normal condition includes the free end moving relative to the spindle.

13. The delivery device of claim 1, further comprising:

a release sleeve assembly disposed between the inner shaft and the delivery sheath assembly, the release sleeve assembly including a release sleeve slidably received over at least a portion of the spindle in the delivery state.

14. The delivery device of claim 13, wherein the release sleeve assembly is configured to proximally retract the release sleeve relative to the spindle with proximal retraction of the delivery sheath distal end from the release sleeve.

15. A system for restoring a defective heart valve of a patient, the system comprising:

a prosthetic heart valve having a stent frame and a valve structure attached to the stent frame, the stent frame defining a distal region and a proximal region, the proximal region forming at least one post; and a delivery device comprising:

a delivery sheath assembly terminating at a distal end and defining a lumen, an inner shaft slidably disposed within the lumen, a capture assembly for selectively coupling the prosthetic heart valve relative to the inner shaft, the capture assembly including:

a spindle attached to the inner shaft, the spindle defining at least one longitudinal capture slot, at least one biasing member disposed within the at least one capture slot and configured to self-transition from a deflected condition to a normal condition, wherein a radial projection of the biasing member relative to a centerline of the inner shaft is greater in the normal condition than in the deflected condition;

wherein the system is configured to provide a loaded mode in which the prosthetic heart valve is retained within the delivery sheath assembly and to the inner shaft, including the at least one post slidably captured within the at least one capture slot and forcing the at least one biasing member to the deflected condition, the at least one post disposed between the delivery sheath assembly and the at least one biasing member in the loaded mode.

16. The system of claim 15, wherein the at least one capture slot includes a plurality of circumferentially spaced capture slots formed in the spindle.

17. The system of claim 16, wherein the at least one biasing member includes a plurality of biasing members disposed within respective ones of the capture slots.

18. The system of claim 15, wherein the spindle includes a distal hub and a proximal flange, the hub and the flange being longitudinally spaced from one another to define a circumferential trough.

19. The system of claim 18, wherein the at least one capture slot is defined in the hub and is open to the trough, and further wherein the at least one biasing member extends across the trough.

20. The system of claim 15, wherein the delivery device further comprises:

a release sleeve assembly disposed between the inner shaft and the delivery sheath assembly, the release sleeve assembly including a release sleeve slidably received over at least a portion of the spindle in the loaded mode.

21. The system of claim 20, wherein the release sleeve is configured to retain a portion of the prosthetic heart valve within the at least one capture slot, causing the portion to force the at least one biasing member to the deflected condition.

22. The system of claim 15, wherein the system is further configured to provide a deployment mode in which the distal end of the delivery sheath is proximal the at least one capture slot and the at least one biasing member self-transitions to the normal condition to eject the at least one post from the at least one capture slot.

* * * * *